United States Patent [19]

Kreisher et al.

[11] Patent Number: 4,588,491
[45] Date of Patent: May 13, 1986

[54] HORIZONTAL GEL ELECTROPHORESIS DEVICE

[75] Inventors: John H. Kreisher, Ridgefield; Hal D. Belle Isle; Charles A. Nalbantian, both of New Haven, all of Conn.

[73] Assignee: International Biotechnologies, Inc., New Haven, Conn.

[21] Appl. No.: 584,138

[22] Filed: Feb. 27, 1984

[51] Int. Cl.[4] .............................................. G01N 27/28
[52] U.S. Cl. .............................. 204/299 R; 204/182.8
[58] Field of Search ............. 204/299 R, 180 G, 182.8

[56] References Cited

U.S. PATENT DOCUMENTS

| | | | |
|---|---|---|---|
| 3,047,489 | 7/1962 | Raymond | 204/299 R |
| 3,374,166 | 3/1968 | Raymond | 204/180 G |
| 3,751,357 | 4/1973 | Rains | 204/299 R |
| 3,873,433 | 3/1975 | Seidel et al. | 204/180 G |
| 4,151,065 | 4/1979 | Kaplan et al. | 204/299 R |
| 4,234,400 | 11/1980 | Kaplan et al. | 204/180 G |

OTHER PUBLICATIONS

International Biotechnologies Inc., 1983 Catalog.

*Primary Examiner*—Howard S. Williams
*Assistant Examiner*—B. J. Boggs, Jr.
*Attorney, Agent, or Firm*—Bachman & LaPointe

[57] ABSTRACT

This application discloses a horizontal gel slab electrophoresis device comprised of a base containing two buffer chambers having a central divider means positioned below a horizontal self. The horizontal shaft is provided with means for cooling. A movable gel tray is positioned on top of the shelf for containing the gel slab and samples to be analyzed. An electrode is positioned in each buffer chamber adjacent to the central divider means. A valve means is positioned in the central divider means for controlling fluid flow between the buffer chambers. In addition, a port is positioned in each buffer chamber for feeding fluids into each of the buffer chambers.

The device is useful in the electrophoresis analysis of samples contained in the gel slab within the movable gel tray.

19 Claims, 5 Drawing Figures

HORIZONTAL GEL ELECTROPHORESIS DEVICE

This invention relates to a horizontal gel electrophoresis device. More particularly, it relates to a horizontal gel slab electrophoresis device having electrodes positioned underneath a horizontal shelf adjoining two buffer chambers in the base of the device.

Numerous electrophoresis devices have been developed since the discovery that charged particles suspended between the poles of an electrical field tend to travel toward the pole that bears a charge opposite the charge of the particle. A number of factors affect the rate of travel, including characteristics of the particle, properties of the electrical field, and environmental factors such as temperature and the nature of the suspending medium.

Commercial devices normally utilize a vertical gel slab containing samples of the colloid or ions to be analyzed for. The distance traveled in a vertical direction when subjected to an electrical field is utilized to determine the components of the samples.

More recently efforts have been made to develop a horizontal gel electrophoresis device for analyzing solutions for colloidal particles or ionic components. For example, U.S. Pat. No. 4,151,065, which issued Nov. 18, 1980, discloses a horizontal gel slab electrophoresis device which has buffer chambers at each end of the device which are separated by a horizontal shelf. Electrodes are positioned within each of the buffer compartments, and a removable gel tray is placed on the shelf. A gel slab is formed within the confines of the tray and removable end pieces are removed after the gel has solidified.

Wicks are poured into the buffer compartments for contacting the exposed ends of the gel slabs. When a current is applied, the current passes from the electrode through the buffer chamber to the wicks, then to the gel slab, and out the opposite buffer chamber in the opposite manner. Movement of the particles through the gel slab is then established and the results may be photographed for permanent record. Although this device has been found to be effective in analyzing for colloidal particles and ionic components, the device needs improvement with respect to the ability to circulate buffer within the buffer chambers, casting of acrylamide gels in place, improvement in the stability of the device, and ease with which the electrodes can be replaced when damaged.

It is a primary object of this invention to provide an improved horizontal gel slab electrophoresis device.

Another object of this invention is to provide improved means for circulating fluids within the buffer chambers of horizontal gel slab electrophoresis devices.

A still further object of the invention is to provide an improved technique for replacing electrodes in horizontal gel slab electrophoresis devices.

Another object is to provide a nitrogen plenum chamber for casting acrylamide gels within the electrophoresis device.

A further object of the invention is to provide an improved top for horizontal gel slab electrophoresis devices.

Another object of this invention is to provide an improved leveling mechanism for obtaining level gel slabs in the detection tray of a horizontal gel slab electrophoresis device.

These and other objects of the invention will be apparent from the following detailed description thereof.

It has been discovered that the foregoing objects are accomplished in a horizontal gel electrophoresis device comprised of two buffer chambers, a generally flat shelf positioned between said buffer chambers and a movable gel tray positioned on said shelf for containing gel and analyzing samples, an electrode in each buffer chamber, and a removable top for said buffer chambers, characterized by the improvement which comprises in combination, a central divider means positioned below said shelf and separating each of said buffer chambers, a valve means in said central divider means for controlling fluid flow between said buffer chambers, and a port in each of said buffer chambers for feeding fluids into said buffer chambers.

Figure 1:
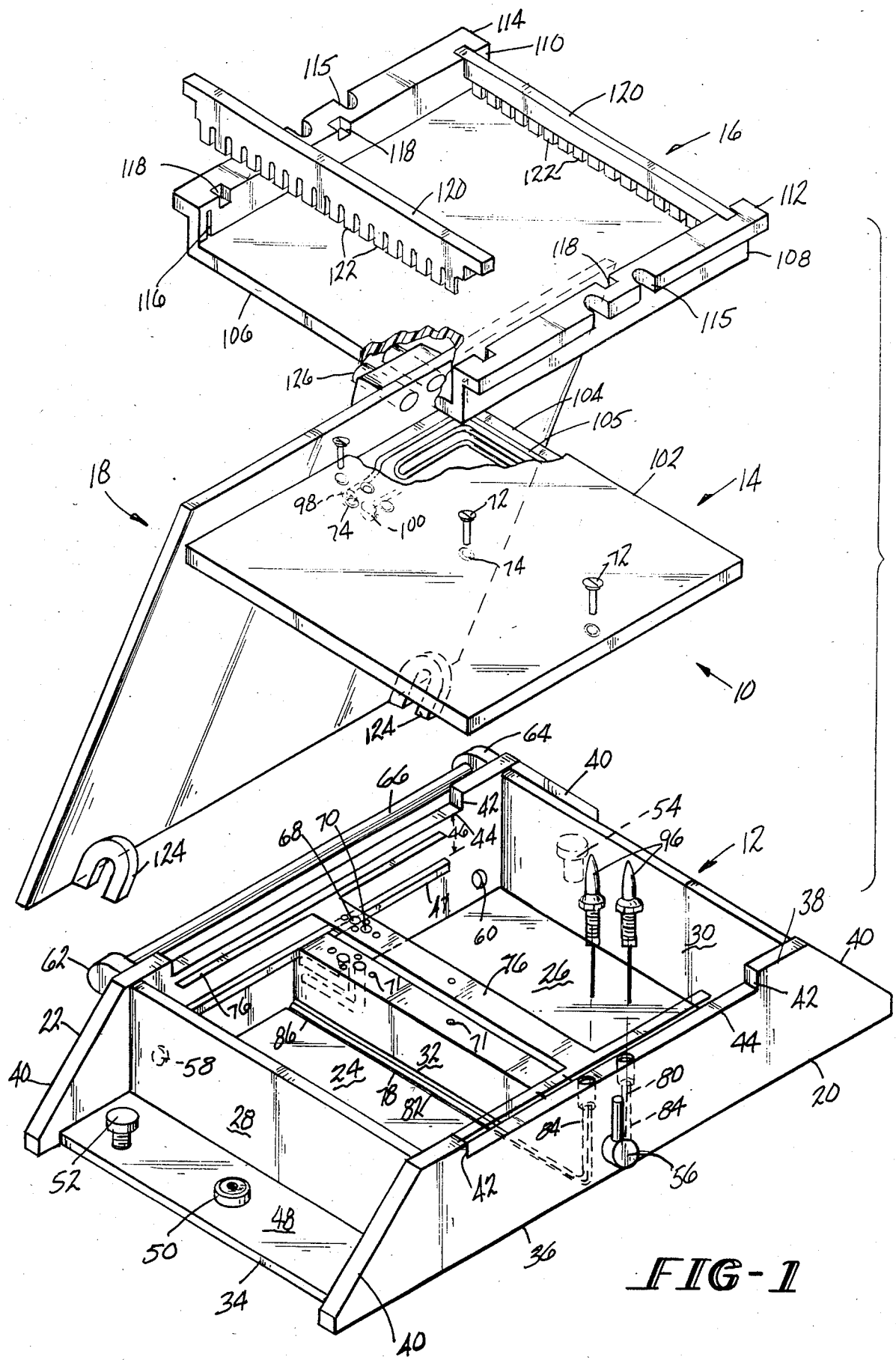
FIG. 1 is an exploded isometric view of the horizontal gel slab electrophoresis device of this invention.
Figure 2:
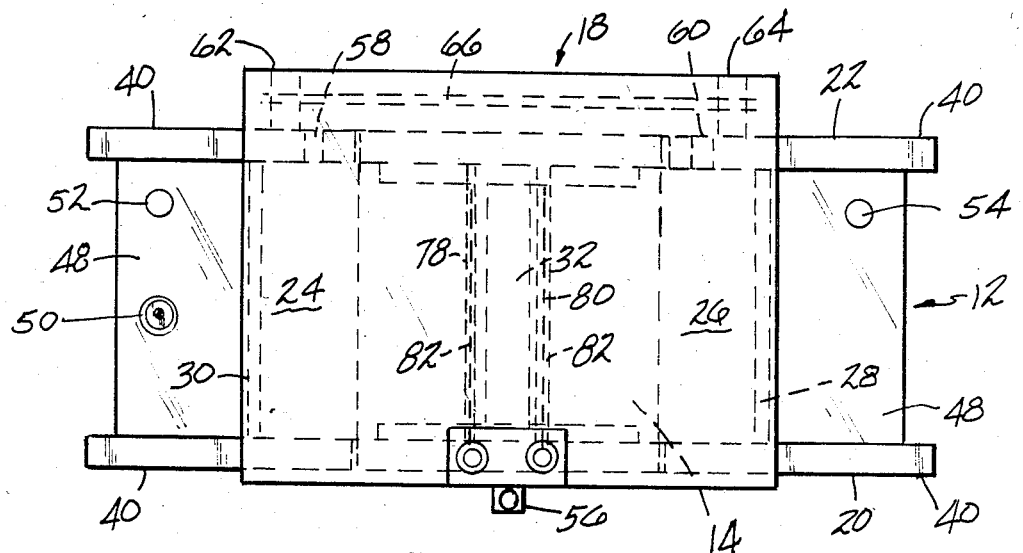
FIG. 2 is a top view of the novel electrophoresis device of this invention.
Figure 3:
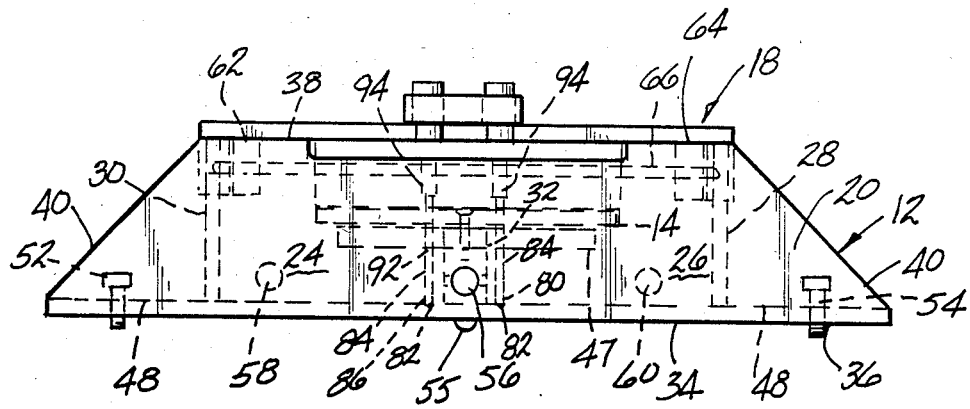
FIG. 3 is a side elevational view of the electrophoresis device of this invention.
Figure 4:
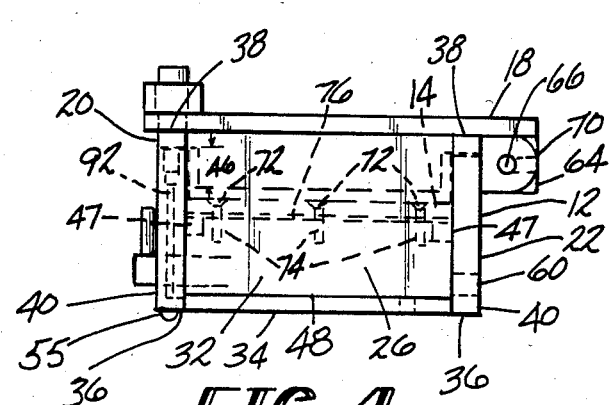
FIG. 4 is an end elevational view of the electrophoresis device of this invention.

More in detail, FIG. 1 shows an exploded isometric view of the horizontal gel slab electrophoresis device 10 of this invention, which is comprised of four major components, device base 12, shelf 14, movable gel tray 16 and removable top 18. FIGS. 2-4 also show these components in top, side and end elevational views, respectively.

As shown in the figures, device base 12 is comprised of a front panel 20 and a rear panel 22, which are two parallel trapezoidal shaped sides, not only providing support for the device base 12, but also forming two opposite parallel sides of buffer chambers 24 and 26. Panels 20 and 22 are positioned perpendicular to bottom 34. Buffer chambers 24 and 26 are also formed by ends 28 and 30, respectively, and central divider means 32 which are each secured perpendicular to bottom 34 and substantially parallel to each other. It is preferred to utilize buffer chambers 24 and 26 of substantially the same volume, but different volumes may be employed, if desired.

Front panel 20 and rear panel 22 are substantially the same dimensions having a base edge 36 substantially longer than top edge 38. Each top edge and base edge are joined by angle edges 40. Each top edge 38 is indented a distance shown by tray leg 42 in order to receive removable gel tray 16 as described more fully below.

Central divider means 32 is positioned perpendicular to bottom 34 and is below tray edge 44 by a distance of shelf leg 46. Extending from central divider means 32 are two pairs of support arms 47 which provide shelf stability.

Ends 28 and 30 are secured to bottom 34 at a point adjacent to where angle edges 40 meet top edges 38. Indenting ends 28 and 30 on bottom 34 in this manner provide base portions 48 where level bubble 50 and leveling screws 52 and 54 are positioned. A leveling pin 55 is positioned on the underside of bottom 34 at a point underneath central divider means 32. With leveling pin 55 in this position, adjustment of leveling screws 52 and 54 can be utilized to position the level bubble in the center and still attain a stationary base when removable top 18 is closed on top of the device base 12.

Valve 56 is secured within central divider means 32 in order to control the flow of fluids between buffer chamber 24 and 26, when desired. Under normal operation, the valve 56 is closed. However, in the event that it is desired to regenerate or equilibrate the buffer solution contained in the chambers, valve 56 is opened and circulation of the buffer in the buffer chambers is effected with a suitable pump (not shown).

Port 58 and port 60 are positioned in buffer chambers 24 and 26, respectively, in rear panel 22 in order to permit the feeding of additional buffer in either chamber and also to permit, when the valve 56 is in the open position, the circulation of buffer solution by suitable pumping means (not shown). In addition, nitrogen may be feed to buffer chambers 24 and 26 when acrylamide type gels, and the like are utilized in movable gel tray 16, as discussed more fully below.

Secured to the exterior of rear panel 22 are two hinge rod holders 62 and 64 having a rod receiving opening in one side thereof in order to hold hinge rod 66.

Central divider means 32 is provided with two openings 68 and 70 which communicate with openings in the rear panel 22 (not shown) for feeding circulating fluid into shelf 14. Screw holes 71 are provided in central divider means 32 which are threaded in order to receive screws 72 for attaching shelf 14 to central divider means 32 in holes 74. The removable shelf 14 allows for ready servicing and maintenance. A gasket 76 is also provided for positioning between the upper face of central divider means 32 and support arms 47, and the bottom of shelf 14 in order to prevent the flow of fluid or electrical charge between buffer chambers 24 and 26 other than through control valve 56.

Two electrodes, generally platinum wires, 78 and 80 are positioned in buffer chambers 24 and 26, respectively. Each electrode has a horizontal section 82 and a non-exposed vertical section 84 shown in the dotted line in FIG. 1. The horizontal portion is tacked by spot sealing or otherwise in groove 86 in the upper surface of bottom 34.

Figure 5:
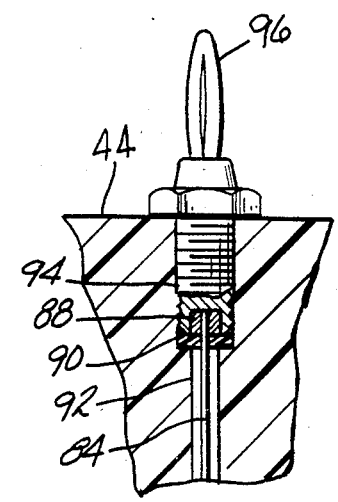
FIG. 5 is a cross sectional view of the electrode attachment means of the electrophoresis device of this invention.

As shown in FIG. 5, vertical section 84 of each electrode has an upper end which is placed inside of a rod 88 having a gasket 90 on the lower portion. Rod 88 and the upper end of vertical section 84 are placed in electrode hole 92 and a threaded bolt-like connector 96, hereinafter referred to as a banana connector 96, is placed in electrode hole 92. Banana connector 96 has an opening 94 in the lower end to receive rod 88 and upper end of vertical section 84. Banana connector 96 is pressed tightly by threads against tray edge 44 to make a firm electric contact with the upper end of vertical section 84. These banana connectors 96 not only firmly secure electrodes 78 and 80 in the device base 12, but also provide easy contact and connection with appropriate wires to receive power for operating the electrophoresis device 10.

Device base 12 shown in FIGS. 1-4 is normally constructed of an appropriate synthetic material such as acrylic, polyvinyl chloride, or similar types of plastic. Transparent chemical resistant plastics of this type are preferred since it is possible to observe and photograph the operation of the electrophoresis device 10 during operation.

Referring to FIGS. 1-4, shelf 14 is comprised of a sandwich of acrylic or other chemically inert polymer, alumina, ceramics or other non-electrical conductive material such as aluminum coated with a non-electrical conductive material. The upper sheet 102 of the sandwich is flat and lower sheet 104 is provided with grooves 105 which are milled to provide a circulatory path for a coolant which is fed to shelf 14 during operation of the electrophoresis unit 10. Shelf 14 is provided with holes 98 and 100 which match holes 68 and 70, respectively, in central divider means 32 for receiving and discharging cooling fluid. The fluid enters the opening (not shown) in the outside surface of rear panels 22 through hole 68 in central divider means 32 and gasket 76 into hole 98. The width of shelf 14 corresponds to the distance between the interior of front panel 20 and the interior of rear panel 22 to provide a stationary horizontal shelf for the movable gel tray 16. The length of shelf 14 is somewhat shorter than the distance between ends 28 and 30 in order to provide sufficient room to operate the cell under conventional wicking conditions as disclosed in the above-mentioned U.S. Pat. No. 4,151,065. When shelf 14 is placed on top of gasket 76 and secured to central divider means 32 by means of screws 72, there is a fluid tight separation of the fluids that are present in buffer chambers 24 and 26. At the same time, flow of the coolant liquid through holes 68 and 98 into grooves 105, through the circulatory path and out holes 100 and 70, while cooling the buffer and gel. This is effected without causing contamination of the buffer solution or other fluid that may be present.

In addition, shelf 14 protects the horizontal sections 82 of electrodes 78 and 80. As a result, the electrodes 78 and 80 may be subjected to extended periods of operation without the need for replacing the electrodes. In addition, it is a relatively simple matter to replace damaged electrodes by removing banana connectors 96 and withdrawing the damaged platinum wire electrodes through the electrode holes 92 and replacing any damaged electrodes with new ones.

Movable gel tray 16 is comprised of a transparent ultraviolet light-transmittant flat bottom portion 106 and two raised sides 108 and 110, which are secured to the sides in parallel fashion perpendicular to flat bottom portion 106. Each raised side 108 and 110 has a flat flanged portion 112 and 114, respectively, which fits into the tray edge 44 of front panel 20 and rear panel 22, respectively. The length of movable gel tray 16 corresponds to the length of shelf 14 and tray 16 is adapted to rest thereon.

Each flange 112 and 114 of movable gel tray 16 is provided with a plurality of tray electrode openings 115 to permit the surrounding of the banana connectors 96 that are positioned vertically in front panel 20. By having such openings 115 in each of the flanges, it is possible to put the movable gel tray 16 onto shelf 14 in either direction without having concern for the location of the electrodes. Since the detecting medium is frequently in liquid form when the movable gel tray 16 is placed into the device, it is sometimes inconvenient to turn the movable gel tray in the opposite direction when placing it in the electrophoresis device 10.

Raised sides 108 and 110 of movable gel tray 16 are provided with a pair of vertical slots 116 which are positioned near the ends of each of the raised sides 108 and 110. In addition, three pairs of comb grooves 118 are positioned near each end and in the center of the raised sides 108 and 110 to permit the insertion of sample combs 120. Each sample comb 120 is provided with a number of sample teeth 122 which may range from about 1 to about 30, or more, depending upon the size of the movable gel tray and the capacity of the electrophoresis device 10. The depth of sample teeth 122 are sufficient to maintain a small level of gel of about 1 mm on the movable gel tray surface 16, and still provide wells for adding samples to the gel after it forms.

The removable top 18 is a generally rectangular cover prepared from the same transparent and ultraviolet transmittant chemical resistant material as removable tray 16 is prepared from. However, the thickness of top 18 is sufficient to render it impervious to strong beta irradiation. Generally a thickness of ¼" or more is satisfactory. Two curved open ended hinges 124 are secured on one interior side of the removable top 18 for inserting over rod 66 and for permitting rotation of the removable top about rod 66. Hinges 124 permit top 18 to completely cover buffer chambers 24 and 26. On the opposite side of top 18 from where hinges 124 are located, there are positioned two top electrode openings 126 to permit closing of the top, and to provide access to the tops of banana connectors 96 for power source connections. A suitable power source is then connected to banana connectors 96 to provide power for operation of the electrophoresis device, when desired.

When top 18 is placed in an open position, the curved hinges position the top at approximately a 90° angle to the horizontal. In such a position, top 18 provides a shield for radiation that may be present in the samples being tested and provides the operator with protection during such operation. In addition, when top 18 is in a closed position, it is easily leveled by leveling screws 52 and 54. As a result, when one movable gel tray is in electrophoresis device 10 during operation, it is possible, while the first set of samples are being electrophoresed, to put a second movable gel tray 16 on the top 18 and proceed with casting a second gel.

In the method of operating electrophoresis device 10, an appropriate gel is cast in movable gel tray 16 by first placing a piece of masking tape or plastic dam across each end of the tray from side 108 to 110 in order to make a liquid-tight container for the gel components. Any suitable gel such as agarose gel having gel percentages ranging from about 0.2 to about 2.0 percent by weight and preferably from about 0.3 to about 1.5 percent by weight are utilized.

After taping or damming the ends of movable gel tray 16, it may be placed in electrophoresis unit 10 or placed on top of top 18. The entire unit is then leveled with the two leveling screws 52 and 54 until level bubble 50 indicates that the unit is level. The agarose is formed into a solution and poured into the taped tray 16 with combs 20 positioned in comb grooves 118. The gel is allowed to polymerize and the combs are then removed by a wiggling and a lifting motion. After polymerization of the gel, the tapes or dams at each end are removed and the movable gel tray containing the cast gel is then positioned on top of shelf 14 if it is not there already. The portion of the gel which solidifies within slots 116 assists in retaining the gel slab in movable gel tray 16 during handling.

A suitable electrophoresis buffer is then added to buffer chambers 24 and 26 in a quantity sufficient to fill the unit to a level that is from about 1 to about 5 millimeters above the gel surface. Samples to be analyzed are then carefully injected into the sample wells formed by the sample teeth 122 of the removed combs 120, taking care not to load the sample on top of the gel. Removable top 18 is then closed and power leads are connected to banana connectors 96. The power supply is turned on and the run is allowed to begin.

A suitable dye such as bromphenol blue is added to the sample solution prior to loading in order to provide a suitable indication during the operation of the electrophoresis unit 10 of the sample analysis. As the power supply operates on the samples, the migration of the dye is followed and the power supply is turned off when migration is complete. The cables are disconnected from the banana connectors 96, the removable top 18 is opened and the movable gel tray containing the gel and samples is removed from the shelf 14. Sample analysis is made by conventional procedures.

If desired, acrylamide is used as the gel for the analysis of the molecules with molecular weights of less than about $1 \times 10^6$ daltons. The small pore size of the acrylamide gives higher resolution to those molecules than that obtained with agarose. Acrylamide gels must be used for protein analysis. In order to cure such a gel, it is poured in the same manner as the agarose gel and placed into the unit, but it must first be cured before operation. Curing is effected by installing a nitrogen supply to both of the ports 58 and 60 in the rear panel 22. Nitrogen is supplied to these ports into the buffer-free unit for a sufficient time, generally from about 30 to about 40 minutes to allow polymerization of the acrylamide gel solution. The combs are then removed from the polymerized gel and operation proceeds, after removing the nitrogen connections, in the same manner as the procedure for the agarose gel.

If desired, buffer may be circulated within unit 10 when it is operated or after in order to equalize the composition. This is effected by opening valve 56 to permit flow of liquid between buffer chamber 24 and buffer chamber 26. At the same time, a suitable pump system is connected to ports 58 and 60 and the pump is turned on in order to circulate buffer solution in the buffer chambers 24 and 26. If desired, the buffer can be reconstituted in an exterior unit and fresh make-up buffer can be placed in the electrophoresis unit.

Trisborate, or trisacetate buffers are most commonly used, but other buffer systems may be used.

Various modifications in the design of the electrophoresis unit 10 described above can be made without departing from the spirit and scope of this invention. One skilled in the art will readily recognize those modifications that can be employed. For example, appropriate wicking gels can be placed at each end of shelf 14 in buffer chambers 24 and 26 and an appropriate conductor paper or gel may be extended between the two wicking units. The cell can then be operated in accordance with the procedure set forth in U.S. Pat. No. 4,234,400, issued Nov. 18, 1980.

If desired, tray 16 can be modified to incorporate a wicking well at each end which is filled with gel along with the flat portion of the tray as described above. Buffer is placed in buffer chambers 24 and 26 to a level to cover the bottom of each wick. Samples and analysis are handled in the manner described above.

Having thus defined the invention, what is desired to be secured by Letters Patent is:

1. A horizontal gel electrophoresis device comprising a generally flat shelf, two side-by-side, horizontally disposed buffer chambers for containing buffer fluid positioned directly beneath said shelf with said shelf running between said chambers to provide buffer fluid directly beneath said shelf, a movable gel tray positioned on said shelf for containing gel and analyzing samples, an electrode in each buffer chamber, a removable top for said buffer chambers, a central divider means positioned directly below said shelf separating each of said buffer chambers and together with said shelf forming a fluid-tight separation therebetween, a valve means in said central divider means for controlling fluid flow between said buffer chambers, and a port in each of said buffer chambers for feeding fluids into said buffer chambers.

2. The device of claim 1 wherein said two buffer chambers are formed from a bottom portion, two parallel sides connected to two parallel ends, and wherein said central divider means is secured between said two parallel sides and said bottom.

3. The device of claim 2 wherein each electrode is comprised of a vertical section connected to a horizontal section, and is positioned adjacent to said central divider means and below said shelf.

4. The device of claim 3 wherein said vertical section of each electrode is secured within one of said sides adjacent to said central divider means.

5. The device of claim 4 wherein each electrode is secured within said side by means of a rod attached to one end of said vertical sections which is positioned within the lower portion of a threaded bolt which is threadably secured against a flexible gasket positioned in the bottom of an electrode opening positioned within said side.

6. The device of claim 4 wherein said horizontal section of each electrode is secured within a groove in the bottom of said buffer chamber adjacent to said central divider means.

7. The device of claim 4 wherein said removable top is provided with hinging means for securing to one of said parallel sides of said buffer chambers.

8. The device of claim 7 including a rod secured to the parallel side opposite from the parallel side in which the electrodes are secured, and slotted hinging means secured to one end of said top for rotating about said rod.

9. The device of claim 1 wherein said tray is provided with vertical slots adjacent to each end to inhibit the flow of gel slab from the tray.

10. The device of claim 1 wherein said parallel sides have a trapezoidal-shaped portion.

11. The device of claim 10 wherein each end of said buffer chambers is secured to the sides at a point removed from said trapezoidal-shaped portion, leaving a bottom portion outside of each buffer chamber.

12. The device of claim 11 wherein a leveling screw is positioned in each bottom portion outside of each buffer chamber.

13. The device of claim 12 wherein a leveling pin is located on the underside of said bottom portion at a point underneath said central dividing means and said vertical portions of said electrodes.

14. The device of claim 13 wherein a leveling bubble is positioned in one of the bottom portions outside of each buffer chamber.

15. The device of claim 1 wherein the buffer chambers covered with said top serves as a nitrogen plenum for casting acrylamide gels in place.

16. The device of claim 1 including cooling means within said shelf for cooling the buffer and gel.

17. The devide of claim 16 including coolant supply means extending through said central divider and into said shelf.

18. The device of claim 17 including coolant removal means extending through said shelf and into said divider.

19. The device of claim 1 including gel and analyzing samples on said tray and buffer fluid in said buffer chambers and covering said gel and analyzing samples.

* * * * *